(12) United States Patent
Ishii

(10) Patent No.: US 9,511,098 B2
(45) Date of Patent: *Dec. 6, 2016

(54) METHOD FOR PRODUCING DRY EARTHWORM POWDER

(75) Inventor: Kazuyuki Ishii, Miyazaki (JP)

(73) Assignee: WELL STONE CO., Miyazaki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/519,346

(22) PCT Filed: Oct. 5, 2011

(86) PCT No.: PCT/JP2011/073017
§ 371 (c)(1),
(2), (4) Date: Jun. 27, 2012

(87) PCT Pub. No.: WO2012/073593
PCT Pub. Date: Jun. 7, 2012

(65) Prior Publication Data
US 2012/0294950 A1    Nov. 22, 2012

(30) Foreign Application Priority Data

Apr. 11, 2011 (JP) ................. 2011-087779

(51) Int. Cl.
A61K 35/24    (2015.01)
A61K 35/37    (2015.01)
A61K 35/12    (2015.01)
A61K 35/62    (2006.01)

(52) U.S. Cl.
CPC .................... *A61K 35/62* (2013.01)

(58) Field of Classification Search
CPC .................... A61K 35/62; A61K 2300/00
USPC ................. 424/520, 537
See application file for complete search history.

(56) References Cited

U.S. PATENT DOCUMENTS 5,024,844 A * 6/1991 Ishii et al. ................ 424/520
5,576,026 A * 11/1996 Charter et al. ............ 424/520
8,137,701 B2 * 3/2012 Ishii et al. ................ 424/520
8,394,417 B2 * 3/2013 Ishii et al. ................ 424/520
2009/0238891 A1 * 9/2009 Ishii et al. ................ 424/520

FOREIGN PATENT DOCUMENTS

| JP | 64-047718 | 2/1989 |
|---|---|---|
| JP | 64-047719 | 2/1989 |
| JP | 64-047720 | 2/1989 |
| JP | 01-268639 | 10/1989 |
| JP | 2-215724 A | 8/1990 |
| JP | 03-072427 | 3/1991 |
| JP | 2006-096673 | 4/2006 |
| JP | 2007-39404 A | 2/2007 |
| JP | 2008-81476 A | 4/2008 |
| JP | 2009-249362 A | 10/2009 |
| RU | 2414918 | 3/2011 |

OTHER PUBLICATIONS

International Search Report for WO2012/073593 A1.
Russian Office Action issued Sep. 24, 2013, 9 pages.

* cited by examiner

*Primary Examiner* — Chris R Tate
*Assistant Examiner* — Russell Fiebig
(74) *Attorney, Agent, or Firm* — Arthur M. Reginelli; Renner, Kenner

(57) ABSTRACT

A method for producing dry earthworm powder, by which dry earthworm powder having high-titer enzymes can be produced while removing toxic substances contained in the bodies of earthworms, is provided. The method comprises:

contacting a live earthworm with a chloride(s) of at least one metal selected from the group consisting of potassium, sodium, magnesium and calcium; and subsequently contacting the live earthworm with powder of a hydroxycarboxylic acid(s) and diluting the resulting mixture with water to adjust pH to 2 to 5, followed by leaving the live earthworm to stand for 3 to 180 minutes, washing the live earthworm with water, grinding the washed live earthworm and freeze-drying the obtained ground product.

12 Claims, No Drawings

METHOD FOR PRODUCING DRY EARTHWORM POWDER

TECHNICAL FIELD

The present invention relates to a method for producing dry earthworm powder, more particularly, a method for producing dry earthworm powder by which dry earthworm powder containing high-titer enzymes can be produced, with toxic substances contained in the body of the earthworm being eliminated.

BACKGROUND ART

Earthworm extracts and dry earthworm powders have been used from ancient times in mainly oriental countries as prophylactic agents and therapeutic agents for various diseases, and examples of their uses so far known include uses as bladder-stone-reducing agents and bladder-stone-excretion-promoting agents, therapeutic agents for icterus, oxytocics, tonics, hair-growing agents, aphrodisiacs, antipyretics, therapeutic agents for convulsion, blood circulation promoters, therapeutic agents for hemiplegia, indirect analgesics, diuretics, therapeutic agents for bronchial asthma and therapeutic agents for hypertension.

However, earthworms, which are kept and bred in cultivation beds, contain toxic elements such as mercury, cadmium, lead and arsenic and pathogenic microorganisms even if carefully selected feeds are given to the earthworms. If these toxic substances are ingested by earthworms and accumulated in their bodies during cultivation, drinking of a therapeutic agent produced from the living bodies of the earthworms may adversely affect a human body.

Therefore, when an agent for oral administration is prepared using living bodies of earthworms as a raw material, these toxic substances must be eliminated, and many methods therefor has been proposed. Examples of the methods proposed so far include methods wherein the living bodies of earthworms are soaked in an aqueous solution of an alkali salt such as a sodium salt or a potassium salt to cause excretion of castings in the digestive tract, followed by wet grinding of the earthworms and vacuum-freeze-drying of the resulting suspension, to produce dry earthworm powder useful as a therapeutic agent for diabetes mellitus, an antihyperlipemic agent or an agent for blood pressure regulation (see Patent Documents 1 to 4); and a method wherein the living bodies of earthworms are left to stand in an aqueous solution of an acid kept at 6 to 26° C. for 0.1 to 5 hours to eliminate castings in the digestive tract, followed by grinding the earthworms, degassing the resulting ground product, and then vacuum-drying the degassed product while increasing the temperature in a stepwise manner, to produce a therapeutic agent for patients suffering from thrombosis (see Patent Document 5).

Further, a method wherein, in order to remove or reduce heavy metals and fibrinolytic activity-suppressing substances, and precursors of the platelet-activating factor, dry earthworm powder is made into an aqueous solution and turbid components are removed therefrom, to obtain an aqueous earthworm solution having a turbidity of not more than 1.5 in terms of an absorbance at a wavelength of 700 nm has been proposed (see Patent Document 6).

RELATED ART DOCUMENTS

Patent Documents

Patent Document 1: Japanese Unexamined Patent Application Publication No. H1-47718
Patent Document 2: Japanese Unexamined Patent Application Publication No. H1-47719
Patent Document 3: Japanese Unexamined Patent Application Publication No. H1-47720
Patent Document 4: Japanese Unexamined Patent Application Publication No. H1-268639
Patent Document 5: Japanese Unexamined Patent Application Publication No. H3-72427
Patent Document 6: Japanese Unexamined Patent Application Publication No. 2006-96673

SUMMARY OF THE INVENTION

Problems to be Solved by the Invention

However, soaking of a living body of an earthworm in fresh water, an aqueous alkali salt solution or an aqueous acid solution for a long time may cause physical exhaustion of the earthworm, resulting in denaturation of proteins contained in the living body and decrease in enzymatic actions, leading to deterioration of pharmacological effects of the obtained earthworm powder. Further, if an earthworm died in the presence of water, the body of the earthworm is rapidly dissolved due to actions of fibrinolytic enzymes existing in the earthworm, and decays. Therefore, the processing in an aqueous solution needs to be carried out under time pressure, which is problematic.

Thus, the present invention aims to provide a method for producing dry earthworm powder, by which dry earthworm powder containing high-titer enzymes can be produced, with toxic substances contained in the body of the earthworm being eliminated.

The present inventors intensively studied to solve the above problems, and discovered that the above problems can be solved by contacting a live earthworm with a chloride(s) of a metal(s), followed by contacting the live earthworm with a hydroxycarboxylic acid(s), thereby completing the present invention.

Means for Solving the Problems

That is, the method of the present invention for producing dry earthworm powder comprises:
contacting a live earthworm with a chloride(s) of at least one metal selected from the group consisting of potassium, sodium, magnesium and calcium; and
subsequently contacting the live earthworm with powder of a hydroxycarboxylic acid(s) and diluting the resulting mixture with water to adjust pH to 2 to 5, followed by leaving the live earthworm to stand for 3 to 180 minutes, washing the live earthworm with water, grinding the washed live earthworm and freeze-drying the obtained ground product.

Further, the method of the present invention for producing dry earthworm powder comprises:
contacting a live earthworm with a chloride(s) of a metal(s) selected from the group consisting of potassium, sodium, magnesium and calcium; and
subsequently soaking the live earthworm in an aqueous solution of a hydroxycarboxylic acid(s) whose pH was adjusted to 2 to 5, followed by leaving the live earthworm to stand for 3 to 180 minutes, washing the live earthworm with water, grinding the washed live earthworm and freeze-drying the obtained ground product.

Preferably, in the method of the present invention for producing dry earthworm powder, the live earthworm is left to stand in a bright place for 10 to 50 hours and dirt attached to the body surface is then peeled off, before the contacting with a chloride(s) of a metal(s).

Further, in the method of the present invention for producing dry earthworm powder, the freeze-drying is preferably carried out by freezing the ground product at −18° C. to −35° C. for 20 to 240 hours and then freeze-drying the resulting product under vacuum.

Further, in the method of the present invention for producing dry earthworm powder, the chloride of a metal is preferably sodium chloride.

Further, in the method of the present invention for producing dry earthworm powder, the hydroxycarboxylic acid(s) is/are at least one selected from the group consisting of acetic acid, malic acid, citric acid, lactic acid, malonic acid and succinic acid.

Effect of the Invention

By the present invention, it is possible to provide a method for producing dry earthworm powder, by which dry earthworm powder containing high-titer enzymes can be produced, with toxic substances contained in the body of the earthworm being eliminated.

MODES FOR CARRYING OUT THE INVENTION

In the method of the present invention for producing dry earthworm powder, a live earthworm is contacted with a chloride(s) of at least one metal selected from the group consisting of potassium, sodium, magnesium and calcium, which is followed by contacting the live earthworm with powder of a hydroxycarboxylic acid(s), diluting the resulting mixture with water to adjust pH to 2 to 5 and leaving the live earthworm to stand for 3 to 180 minutes; or soaking the live earthworm in an aqueous solution of a hydroxycarboxylic acid(s) whose pH was adjusted to 2 to 5 and leaving the live earthworm to stand for 3 to 180 minutes; which earthworm is then washed with water and ground, followed by freeze-drying the obtained ground product.

By contacting the live earthworm with the predetermined metal chloride(s) and then with the hydroxycarboxylic acid(s) before processing the earthworm, a habitat uncomfortable to the earthworm is formed, and as a result, the earthworm excretes digests in the digestive tract to adapt to the environment, and at the same time, toxic substances such as mercury, cadmium and lead contained in the body are excreted.

Methods wherein environments uncomfortable to earthworms are formed to make an earthworm vomit feces and the like containing toxic substances in the body of the earthworm, followed by grinding the earthworm have been known. The present invention was made based on discovery that combining specific methods, among the above methods, for forming uncomfortable environments and performing these methods in a specific order enable production of dry earthworm powder having excellent enzymatic activities. That is, what is important is that a metal chloride(s) (the osmotic stress) and a hydroxycarboxylic acid(s) (the pH stress) are given in that order.

Although molecular biological analysis has not been progressed well in earthworms and detailed mechanisms are hence not necessarily clear, the osmotic stress is known to activate transcription of various stress response genes such as heat shock protein genes, in researches of other model organisms such as yeasts, nematodes and plants. Therefore, one of the reasons why the effect of the present invention can be obtained may be, for example, that HSP genes and the like are first activated by the osmotic stress, and subsequently, the earthworm is further subjected to another stress, the pH stress, which causes further activation of the expression pathways of stress response genes, leading to remarkable enhancement of the production amounts of useful enzymes.

In the method of the present invention, a live earthworm, that is, an earthworm which is alive, is used. The live earthworm is not restricted, and examples thereof include *Lumbricus rubellus, Lumbricus terrestris, Eisenia foetida, Allolobophora caliginosa, Dendrobaena octaedra, Allolobophora japonica* Michaelsen, *Drawida hattamimizu* Hatai, *Pheretima divergens* Michaelsen, *Pheretima communissima, Pheretima agrestis, Pheretima sieboldi* Horst, *Pheretima hilgendorfi, Pontodrilus matsushimensis* Iizuka, *Tubifex hattai* Nomura and *Limnodrilus gotoi* Hatai (=*L. Socialis* Stephenson).

In the method of the present invention, before the contacting of live earthworms to a metal chloride(s), the live earthworms are preferably placed in a flat container such as a bread container and left to stand in a bright place for 10 to 50 hours, followed by removing dirt attached to the body surfaces. The length of time during which the earthworms are left to stand in a bright place is more preferably 12 to 24 hours. The amount of the earthworms is preferably an amount with which the earthworms are piled up to attain a thickness of about 30 to 60 mm, preferably about 40 to 50 mm. This flat container is made free from foreign substances such as sand and mud, and the inside of the container is preferably kept bright at night by light cultivation or the like since earthworms are nocturnal and their daily activity becomes active in a dark place, leading to physical exhaustion. By this procedure, earthworms exert their self-protective instinct and excrete digests remaining in the digestive tract, with which their whole bodies are covered to prevent evaporation of water and thereby to maintain their living environment. Therefore, by repeating peeling off this covering dirt, that is, excrement, by an appropriate method, digests in the digestive tract and dirt attached to the body surfaces can be finally removed.

The dirt attached to the body surfaces of earthworms can be peeled off by, for example, covering live earthworms with a non-woven fabric to allow adsorption of dirt thereto. By combining this leaving of the earthworms to stand in a bright place followed by removal of dirt attached to the body surfaces and contacting of the earthworms with a metal chloride(s) and a hydroxycarboxylic acid(s), excretion and removal of toxic substances in the bodies of the earthworms can be further expected.

The metal chloride(s) used in the present invention is/are a chloride(s) of at least one metal selected from the group consisting of potassium, sodium, magnesium and calcium. That is, the metal chloride(s) is/are at least one selected from the group consisting of potassium chloride, sodium chloride, magnesium chloride and calcium chloride. Further, the metal chloride(s) may be either their mixture or a mixture of these and other harmless components which can be added to food. Examples of such a mixture include dietary salts, rock salts and bay salts. The above-described metal chloride(s) may be used by sprinkling its/their powder on live earthworms, and this causes contact of the metal chloride(s) with the earthworms.

After contacting metal chloride(s) with live earthworms, the live earthworms are brought into contact with a hydroxycarboxylic acid(s). The contacting with the hydroxycarboxylic acid(s) can also be carried out by sprinkling powder of the hydroxycarboxylic acid(s) on the live earthworms. The contacting with the hydroxycarboxylic acid(s) is carried out immediately after the contacting with the above-described metal chloride(s). Further, before bringing the live earthworms to contact with a hydroxycarboxylic acid(s), the earthworms are preferably washed with water. Removing the metal chloride(s) by washing with water followed by bringing the live earthworms into contact with a hydroxycarboxylic acid(s) enables production of dry earthworm powder having high enzymatic activities. In cases where the earthworms are washed with water before being brought into contact with a hydroxycarboxylic acid(s), the washing of earthworms with water is carried out preferably within 30 minutes, more preferably within 20 minutes, after beginning of the contacting with a metal chloride(s). The method of washing with water is not restricted, and a known method may be employed.

If live earthworms are kept in contact with powder of a hydroxycarboxylic acid(s) for a long time, their vital functions are lost, and digests in the digestive tract are not excreted. Therefore, the hydroxycarboxylic acid(s) need(s) to be diluted with water as soon as possible, preferably within 30 seconds, more preferably within 20 seconds, to adjust pH to 2 to 5.

Since the hydroxycarboxylic acid(s) form(s) a living environment uncomfortable to earthworms, the live earthworms try to improve the living environment by excretion of their body fluids and excrement due to their self-protective instinct. Further, since hydroxycarboxylic acids have bactericidal properties, they are expected to play a role not only in promotion of excretion of digests and the like remaining in the digestive tract as described above, but also in killing bacteria attached to the earthworms.

The crystalline hydroxycarboxylic acid used in the method of the present invention is not restricted by the numbers of its hydroxy groups and carboxyl groups, as long as they are in the forms of crystalline bodies under the service conditions. That is, the crystalline hydroxycarboxylic acid may be any of monohydroxy monocarboxylic acid, monohydroxy polycarboxylic acid, polyhydroxy monocarboxylic acid and polyhydroxy polycarboxylic acid.

Examples of the hydroxycarboxylic acid(s) used in the present invention include glycolic acid, lactic acid, acetic acid, β-hydroxypropionic acid, α-hydroxy-n-butyric acid, β-hydroxy-n-butyric acid, α-hydroxy-n-valeric acid, β-hydroxy-n-valeric acid, malic acid, α-methylmalic acid, α-hydroxyglutaric acid, β-hydroxyglutaric acid, citric acid, malonic acid and succinic acid. Among these, lactic acid, acetic acid, malic acid, citric acid, malonic acid and succinic acid are preferred in view of the fact that these may be used in food and can be easily obtained. A single type of hydroxycarboxylic acid may be used alone, or a mixture of 2 or more types thereof may be used.

Water accounts for 65% of the total components of tissues of a live earthworm. Although the protective functions of a live earthworm are effective for a certain length of time, death of the live earthworm allows enzymes to act, so that the length of time during which the live earthworm is placed under an uncomfortable environment needs to be carefully controlled. The length of time varies depending on the conditions, and is usually within the range of 3 to 180 minutes.

In the present invention, the live earthworms processed with a hydroxycarboxylic acid(s) are washed with water and then ground into a ground product in the form of a liquid or a paste. The washing is preferably carried out with pure water. The method of washing is not restricted, and a known method for washing with water can be employed. Further, the total length of time spent for the steps before the grinding, that is, the total length of time spent for the steps from sprinkling of a metal chloride(s) on live earthworms to finishing washing out of a hydroxycarboxylic acid(s) with water, is preferably not more than 240 minutes.

The method of above-described grinding is not restricted, and, for example, the grinding is carried out using a homogenizer, blender, homomixer, grinder, French press or the like, usually at 1 to 25° C. In view of suppression of degradation of constituting components of earthworms, the grinding is preferably carried out at a low temperature, preferably at a temperature of 2 to 15° C.

The ground product obtained by grinding earthworms is placed on a stainless-steel tray and subjected to freeze-drying. Although enzymes contained in the living body of an earthworm do not act on live cells, they act on dead cells instantly. Therefore, in the above process, there is a risk of generation of septic gases. In order to prevent the generation of septic gases, the ground product is preferably momentarily subjected to freezing by rapid cooling to −18° C. to −35° C. to suppress actions of enzymes, followed by freeze-drying.

Thus, pulverization of earthworms without loss of pharmacological actions needs rapid freezing, but, on the other hand, too rapid freezing is not preferred since, in cases where earthworms are frozen too rapidly, impurities existing together with proteins, which are major components of the earthworm paste, may form unfrozen spots and cannot be separated. Therefore, the freezing is carried out at a low temperature of −18° C. to −35° C. for preferably 20 to 240 hours, more preferably 50 to 170 hours.

It is important for the freeze-drying to select conditions under which impurities can be removed without remaining together with water. Therefore, the freeze-drying is preferably carried out under control at a pressure of not more than 50 Pa at a temperature of −60° C. to +90° C. while increasing the temperature in a stepwise manner for 10 to 60 hours.

Examples of the method of freeze-drying include a method wherein the ground product is frozen as described above at a temperature of −18° C. to −35° C. for 20 to 240 hours, and the temperature is then increased in several steps within the range of −60° C. to +90° C. and the pressure is decreased in several steps within the range of 25 to 40 Pa, while freeze-drying the product under vacuum for 10 to 60 hours, thereby obtaining sterile pale yellow dry earthworm powder.

The thus obtained dry earthworm powder contains, in 100 g of the powder, 70 to 120 mg of arginine, 110 to 150 mg of lysine, 35 to 60 mg of histidine, 55 to 80 mg of phenylalanine, 50 to 75 mg of tyrosine, 100 to 150 mg of leucine, 60 to 90 mg of isoleucine, 25 to 40 mg of methionine, 70 to 105 mg of valine, 85 to 135 mg of alanine, 75 to 105 mg of glycine, 60 to 85 mg of proline, 210 to 300 mg of glutamic acid, 80 to 110 mg of serine, 75 to 110 mg of threonine, 150 to 220 mg of aspartic acid, 15 to 30 mg of tryptophan and 20 to 35 mg of cystine, although their contents vary depending on the type of the earthworms and the site and time of collection of the earthworms.

EXAMPLES

The present invention will now be described below in more detail. The present invention is not restricted to the Examples below.

[Preparation of Dry Earthworm Powder]

Example 1

30 kg of live *Lumbricus rubellus* were left to stand for 24 hours in a bright place, and dirt attached to the body surfaces was peeled off, followed by spreading the earthworms on a flat dish at a thickness of about 5 cm and sprinkling 250 g of sodium chloride uniformly thereon. 20 minutes later, the earthworms were washed with water.

Subsequently, 250 g of citric acid was sprinkled on the earthworms in a similar manner, and the resultant was diluted in 15 seconds thereafter by adding 30 liters of pure water. At this time, pH immediately after the addition of water was 2.25, and pH after the complete dilution was 2.74.

When the citric acid powder was sprinkled, the earthworms released a yellow body fluid at once. After the dilution with water, the earthworms were left to stand in this state for 20 minutes.

Subsequently, the live earthworms were removed from the dirty aqueous citric acid solution and washed with water, followed by being ground using a homogenizer at 10° C., to prepare an earthworm paste. Thereafter, this earthworm paste was degassed by aspiration to remove gases contained therein, and transferred onto a stainless-steel tray, followed by being momentarily and rapidly cooled to −35° C., at which temperature the earthworm paste was maintained for 50 hours to allow slow freezing.

The frozen earthworm paste was maintained at −35° C. at a pressure of 0 Pa for 2 hours, and the temperature was then increased to 25° C., followed by freeze-drying under vacuum at 40 Pa for 10 hours; at 40° C. at a pressure of 35 Pa for 14 hours; at 65° C. at a pressure of 35 Pa for 12 hours; and finally at a temperature of 80° C. at a pressure of 25 Pa for 6 hours. By this treatment, a pale-yellow dry earthworm powder having a moisture content of 8% by mass was obtained.

Comparative Example 1

30 kg of live *Lumbricus rubellus* were left to stand for 24 hours in a bright place, and dirt attached to the body surfaces was peeled off, followed by spreading the earthworms on a flat dish at a thickness of about 5 cm and adding 30 liters of water thereto. Thereafter, the earthworms were left to stand in this state for 20 minutes.

Subsequently, the live earthworms were removed from water and washed with water, followed by being ground using a homogenizer at 10° C., to prepare an earthworm paste. Thereafter, this earthworm paste was degassed by aspiration to remove gases contained therein, and transferred onto a stainless-steel tray, followed by being momentarily and rapidly cooled to −35° C., at which temperature the earthworm paste was maintained for 50 hours to allow slow freezing.

The frozen earthworm paste was maintained at −35° C. at a pressure of 0 Pa for 2 hours, and the temperature was then increased to 25° C., followed by freeze-drying under vacuum at 40 Pa for 10 hours; at 40° C. at a pressure of 35 Pa for 14 hours; at 65° C. at a pressure of 35 Pa for 12 hours; and finally at a temperature of 80° C. at a pressure of 25 Pa for 6 hours. By this treatment, a pale-yellow dry earthworm powder having a moisture content of 8% by mass was obtained.

Comparative Example 2

30 kg of live *Lumbricus rubellus* were left to stand for 24 hours in a bright place, and dirt attached to the body surfaces was peeled off, followed by spreading the earthworms on a flat dish at a thickness of about 5 cm and sprinkling 250 g of citric acid thereon. In 15 seconds thereafter, 30 liters of pure water was added to the resultant for dilution.

When the citric acid powder was sprinkled, the earthworms released a yellow body fluid at once. After the dilution with water, the earthworms were left to stand in this state for 20 minutes.

Subsequently, the live earthworms were removed from the dirty aqueous citric acid solution and washed with water, followed by being ground using a homogenizer at 10° C., to prepare an earthworm paste. Thereafter, this earthworm paste was degassed by aspiration to remove gases contained therein, and transferred onto a stainless-steel tray, followed by being momentarily and rapidly cooled to −35° C., at which temperature the earthworm paste was maintained for 50 hours to allow slow freezing.

The frozen earthworm paste was maintained at −35° C. at a pressure of 0 Pa for 2 hours, and the temperature was then increased to 25° C., followed by freeze-drying under vacuum at 40 Pa for 10 hours; at 40° C. at a pressure of 35 Pa for 14 hours; at 65° C. at a pressure of 35 Pa for 12 hours; and finally at a temperature of 80° C. at a pressure of 25 Pa for 6 hours. By this treatment, a pale-yellow dry earthworm powder having a moisture content of 8% by mass was obtained.

Comparative Example 3

30 kg of live *Lumbricus rubellus* were left to stand for 24 hours in a bright place, and dirt attached to the body surfaces was peeled off, followed by spreading the earthworms on a flat dish at a thickness of about 5 cm and sprinkling 250 g of citric acid thereon. Thereafter, 30 liters of pure water was added to the resultant for dilution. When the citric acid powder was sprinkled, the earthworms released a yellow body fluid at once. After the dilution with water, the earthworms were left to stand in this state for 20 minutes. Subsequently, the live earthworms were removed from the dirty aqueous citric acid solution and washed with water, followed by being sprinkled with 250 g of sodium chloride and left to stand in this state for 20 minutes.

Subsequently, the live earthworms were washed with water and ground using a homogenizer at 10° C., to prepare an earthworm paste. Thereafter, this earthworm paste was degassed by aspiration to remove gases contained therein, and transferred onto a stainless-steel tray, followed by being momentarily and rapidly cooled to −35° C., at which temperature the earthworm paste was maintained for 50 hours to allow slow freezing.

The frozen earthworm paste was maintained at −35° C. at a pressure of 0 Pa for 2 hours, and the temperature was then increased to 25° C., followed by freeze-drying under vacuum at 40 Pa for 10 hours; at 40° C. at a pressure of 35 Pa for 14 hours; at 65° C. at a pressure of 35 Pa for 12 hours; and finally at a temperature of 80° C. at a pressure of 25 Pa for 6 hours. By this treatment, a pale-yellow dry earthworm powder having a moisture content of 8% by mass was obtained.

Comparative Example 4

30 kg of live *Lumbricus rubellus* were left to stand for 24 hours in a bright place, and dirt attached to the body surfaces was peeled off, followed by spreading the earthworms on a flat dish at a thickness of about 5 cm, mixing 250 g of citric acid with 250 g of sodium chloride, and sprinkling the resulting mixture uniformly on the earthworms. In 15 seconds thereafter, 30 liters of pure water was added to the resultant for dilution.

When the citric acid powder and sodium chloride were sprinkled, the earthworms released a yellow body fluid at once. After the dilution with water, the earthworms were left to stand in this state for 20 minutes.

Subsequently, the live earthworms were removed from the dirty aqueous citric acid solution and washed with water, followed by being ground using a homogenizer at 10° C., to prepare an earthworm paste. Thereafter, this earthworm paste was degassed by aspiration to remove gases contained therein, and transferred onto a stainless-steel tray, followed by being momentarily and rapidly cooled to −35° C., at which temperature the earthworm paste was maintained for 50 hours to allow slow freezing.

The frozen earthworm paste was maintained at −35° C. at a pressure of 0 Pa for 2 hours, and the temperature was then increased to 25° C., followed by freeze-drying under vacuum at 40 Pa for 10 hours; at 40° C. at a pressure of 35 Pa for 14 hours; at 65° C. at a pressure of 35 Pa for 12 hours; and finally at a temperature of 80° C. at a pressure of 25 Pa for 6 hours. By this treatment, a pale-yellow dry earthworm powder having a moisture content of 8% by mass was obtained.

[Titration of Dry Earthworm Powder]

<Preparation of Measurement Sample>

To 1 g of each dry earthworm powder obtained as described above, 20 ml of physiological saline was added, the resulting mixture was shaken at 1500 rpm for 1 hour. The mixture was then centrifuged at 10000×g at 4° C. for 15 minutes, and the resulting supernatant was used as a measurement sample.

<Method of Protein Quantification>

In terms of protein quantification, calculation was carried out according to the Bradford method (M. Bradford, Anal. Biochem., 72: 248-254, 1976).

A sample for measurement of the protein mass was prepared for the above measurement sample using a protein assay kit (Bio-Rad Laboratories, Inc.), and the absorbance at 595 nm was measured. Using a calibration curve prepared separately using bovine serum albumin (Bovine, Sigma-Aldrich Co.), the measured value was converted to the protein mass.

TABLE 1

| | Example 1 | Comparative Example 1 | Comparative Example 2 | Comparative Example 3 | Comparative Example 4 |
|---|---|---|---|---|---|
| 1st Measurement | 1.9 | 12.6 | 6.2 | 6.1 | 3.2 |
| 2nd Measurement | 2.0 | 11.1 | 6.1 | 5.6 | 2.9 |
| 3rd Measurement | 1.1 | 11.8 | 5.8 | 5.9 | 3.2 |
| Mean | 1.7 | 11.8 | 6.0 | 5.9 | 3.1 |

<Synthetic Amide Substrate Degradation Method>

According to the method described in a Non-patent Document (Sumi, H., Okamoto, T. and Ishii, Y., Titration Method for Lumbrokinase (Earthworm Enzyme)—Fibrinolytic and Synthetic Amidolytic Activities—, Clinical Pharmacology and Therapy, 20: 347-351, 2010), the synthetic amide substrate degradation activity was measured.

The synthetic amide substrate was prepared by dissolving pyroGlu-Gly-Arg-pNA (BIOPHEN CS-61(44), COSMO BIO Co., Ltd.), which is a synthetic substrate for urokinase, in dimethyl sulfoxide (DMSO) to a concentration of $5 \times 10^{-3}$ M.

To 0.1 ml of the measurement sample obtained as described above, 0.8 ml of borate saline buffer (BSB) was added, and the resulting solution was incubated for 2 minutes, followed by adding 0.1 ml of the synthetic amide substrate to the solution and allowing the reaction to proceed at 37° C. for 5 minutes. Subsequently, the absorbance at 405 nm was measured, and the amount of pNA released was calculated based on the maximum slope (initial rate) per minute, with an absorption coefficient of $10.79 \text{ mM}^{-1} \cdot \text{cm}^{-1}$. The obtained results are shown in Table 2 below.

Further, the synthetic amide substrate degradation activity was divided by the total protein amount to obtain the specific activity, which is shown in Table 3 below.

TABLE 2

| | Example 1 | Comparative Example 1 | Comparative Example 2 | Comparative Example 3 | Comparative Example 4 |
|---|---|---|---|---|---|
| 1st Measurement | 59.2 | 56.3 | 72.8 | 54.9 | 59.9 |
| 2nd Measurement | 59.5 | 53.6 | 79.2 | 56.0 | 60.5 |
| 3rd Measurement | 59.5 | 54.2 | 77.7 | 55.6 | 61.7 |
| 4th Measurement | 63.0 | 56.5 | 82.5 | 65.8 | 66.0 |
| 5th Measurement | 62.1 | 54.7 | 80.6 | 65.8 | 65.5 |
| 6th Measurement | 64.9 | 53.8 | 79.7 | 63.0 | 66.3 |
| Mean | 61.4 | 54.9 | 78.8 | 60.2 | 63.3 |

TABLE 3

| | Synthetic amide degradation activity (n mol/ml/min) | Protein amount (mg/ml) | Specific activity (n mol/ml/min/mg) |
|---|---|---|---|
| Example 1 | 61.4 | 1.7 | 36.1 |
| Comparative Example 1 | 54.9 | 11.8 | 4.7 |
| Comparative Example 2 | 78.8 | 6.0 | 13.1 |
| Comparative Example 3 | 60.2 | 5.9 | 10.2 |
| Comparative Example 4 | 63.3 | 3.1 | 20.4 |

<Fibrin Plate Method>

According to the method described in a Non-patent Document (T. Astrup & S. Mullertz, The fibrin plate method for estimating fibrinolytic activity, Arch. Biochem. Biophys., 40: 346-351, 1952), a fibrin plate was prepared, and comparison of the dissolution activity was carried out by the fibrin plate method.

Fibrinogen (Bovine Fraction I-S, Sigma-Aldrich Co.) was dissolved in borate saline buffer (pH 7.8: BSB) to a final concentration of 0.5%. To 10 ml of this solution, 0.5 ml of thrombin (for clinical use, Fuji Pharma Co., Ltd.) was added, to prepare a fibrin plate.

Measurement of the area of dissolution was carried out by placing 30 µl of each measurement sample on the plate and measuring the area of the dissolved zone which appeared after 4 hours of incubation at 37° C. Further, a calibration curve for trypsin (Bovine, Sigma-Aldrich Co.), which is a protease, was prepared, and unit conversion was carried out to determine the specific activity based on the protein amount in each measurement sample. The results are shown in Table 4 below.

TABLE 4

|  | Dissolved area (mm$^2$) | Activity in trypsin units (U/ml) | Protein amount (mg/ml) | Specific activity (U/mg) |
| --- | --- | --- | --- | --- |
| Example 1 | 223.3 | 287.2 | 1.7 | 168.9 |
| Comparative Example 1 | 211.3 | 256.5 | 11.8 | 21.7 |
| Comparative Example 2 | 272.5 | 462.8 | 6.0 | 77.1 |
| Comparative Example 3 | 259.7 | 414.2 | 5.9 | 70.2 |
| Comparative Example 4 | 171.6 | 156.0 | 3.1 | 50.3 |

By the method of the present invention, a high-quality dry earthworm powder from which toxic substances were removed can be obtained. Further, as is evident from Example 1, the dry earthworm powder produced by the production method of the present invention contains high-titer enzymes.

On the other hand, as is evident from Comparative Examples 1 and 2, the enzymatic activity in the case where only the citric acid treatment was performed was only 2 to 4 times higher than in the case where the treatment was performed with water. Further, as is evident from the results of Comparative Examples 2 and 3, in the case where the citric acid treatment was first carried out and the metal chloride treatment was then carried out, the enzymatic activity was almost the same as in the case where only the citric acid treatment was performed.

Example 2

30 kg of live *Lumbricus rubellus* were left to stand for 24 hours in a bright place, and dirt attached to the body surfaces was peeled off, followed by spreading the earthworms on a flat dish at a thickness of about 5 cm and sprinkling 250 g of magnesium chloride uniformly thereon. 20 minutes later, the earthworms were washed with water.

Subsequently, 250 ml of lactic acid was sprinkled in the same manner, and the resultant was diluted in 15 seconds thereafter by adding 30 liters of pure water. When lactic acid was sprinkled, the earthworms released a yellow body fluid at once. After the dilution with water, the earthworms were left to stand in this state for 20 minutes.

Subsequently, the live earthworms were removed from the dirty aqueous lactic acid solution and washed with water, followed by being ground using a homogenizer at 10° C., to prepare an earthworm paste. Thereafter, this earthworm paste was degassed by aspiration to remove gases contained therein, and transferred onto a stainless-steel tray, followed by being momentarily and rapidly cooled to −35° C., at which temperature the earthworm paste was maintained for 50 hours to allow slow freezing.

The frozen earthworm paste was maintained at −35° C. at a pressure of 0 Pa for 2 hours, and the temperature was then increased to 25° C., followed by freeze-drying under vacuum at 40 Pa for 10 hours; at 40° C. at a pressure of 35 Pa for 14 hours; at 65° C. at a pressure of 35 Pa for 12 hours; and finally at a temperature of 80° C. at a pressure of 25 Pa for 6 hours. By this treatment, a pale-yellow dry earthworm powder having a moisture content of 8% by mass was obtained.

Comparative Example 5

30 kg of live *Lumbricus rubellus* were left to stand for 24 hours in a bright place, and dirt attached to the body surfaces was peeled off, followed by spreading the earthworms on a flat dish at a thickness of about 5 cm, sprinkling 250 ml of lactic acid thereon in the same manner, and diluting the resultant in 15 seconds thereafter by adding 30 liters of pure water. When lactic acid was sprinkled, the earthworms released a yellow body fluid at once. After the dilution with water, the earthworms were left to stand in this state for 20 minutes.

Subsequently, the live earthworms were removed and washed with water, followed by sprinkling 250 g of magnesium chloride uniformly thereon and leaving the earthworms to stand in this state for 20 minutes.

Subsequently, the live earthworms were removed and washed with water, followed by being ground using a homogenizer at 10° C., to prepare an earthworm paste. Thereafter, this earthworm paste was degassed by aspiration to remove gases contained therein, and transferred onto a stainless-steel tray, followed by being momentarily and rapidly cooled to −35° C., at which temperature the earthworm paste was maintained for 50 hours to allow slow freezing.

The frozen earthworm paste was maintained at −35° C. at a pressure of 0 Pa for 2 hours, and the temperature was then increased to 25° C., followed by freeze-drying under vacuum at 40 Pa for 10 hours; at 40° C. at a pressure of 35 Pa for 14 hours; at 65° C. at a pressure of 35 Pa for 12 hours; and finally at a temperature of 80° C. at a pressure of 25 Pa for 6 hours. By this treatment, a pale-yellow dry earthworm powder having a moisture content of 8% by mass was obtained.

[Titration of Dry Earthworm Powder]
<Preparation of Measurement Sample>

To 1 g each of the dry earthworm powders obtained as described above in Example 2 and Comparative Example 5, 20 ml of physiological saline was added, and the resulting mixture was shaken at 1500 rpm for 1 hour. The mixture was then centrifuged at 10000×g at 4° C. for 15 minutes, and the resulting supernatant was used as a measurement sample.

<Method of Protein Quantification>

In terms of protein quantification, calculation was carried out according to the Bradford method (M. Bradford, Anal. Biochem., 72: 248-254, 1976).

A sample for measurement of the protein mass was prepared for the above measurement sample using a protein assay kit (Bio-Rad Laboratories, Inc.), and the absorbance at 595 nm was measured. Using a calibration curve prepared separately using bovine serum albumin (Bovine, Sigma-Aldrich Co.), the measured value was converted to the protein mass.

TABLE 5

|  | Example 2 | Comparative Example 5 |
| --- | --- | --- |
| 1st Measurement | 6.6 | 7.1 |
| 2nd Measurement | 7.0 | 7.8 |
| 3rd Measurement | 7.0 | 7.0 |
| Mean | 6.9 | 7.3 |

<Synthetic Amide Substrate Degradation Method>

According to the method described in a Non-patent Document (Sumi, H., Okamoto, T. and Ishii, Y., Titration Method for Lumbrokinase (Earthworm Enzyme)—Fibrinolytic and Synthetic Amidolytic Activities—, Clinical Pharmacology and Therapy, 20: 347-351, 2010), the synthetic amide substrate degradation activity was measured.

The synthetic amide substrate was prepared by dissolving pyroGlu-Gly-Arg-pNA (BIOPHEN CS-61(44), COSMO BIO Co., Ltd.), which is a synthetic substrate for urokinase, in dimethyl sulfoxide (DMSO) to a concentration of $5 \times 10^{-3}$ M.

To 0.1 ml of the measurement sample obtained as described above, 0.8 ml of borate saline buffer (BSB) was added, and the resulting solution was incubated for 2 minutes, followed by adding 0.1 ml of the synthetic amide substrate to the solution and allowing the reaction to proceed at 37° C. for 5 minutes. Subsequently, the absorbance at 405 nm was measured, and the amount of pNA released was calculated based on the maximum slope (initial rate) per minute, with an absorption coefficient of $10.79 \text{ mM}^{-1} \cdot \text{cm}^{-1}$. The obtained results are shown in Table 6 below.

Further, the synthetic amide substrate degradation activity was divided by the total protein amount to obtain the specific activity, which is shown in Table 7 below.

TABLE 6

|  | Example 2 | Comparative Example 5 |
| --- | --- | --- |
| 1st Measurement | 71.1 | 41.5 |
| 2nd Measurement | 73.7 | 41.4 |
| 3rd Measurement | 72.0 | 42.3 |
| 4th Measurement | 73.6 | 44.4 |
| 5th Measurement | 73.7 | 43.8 |
| 6th Measurement | 70.6 | 41.6 |
| Mean | 72.5 | 42.5 |

TABLE 7

|  | Synthetic amide degradation activity (n mol/ml/min) | Protein amount (mg/ml) | Specific activity (n mol/ml/min/mg) |
| --- | --- | --- | --- |
| Example 2 | 72.5 | 6.9 | 10.5 |
| Comparative Example 5 | 42.5 | 7.3 | 5.8 |

<Fibrin Plate Method>

According to the method described in a Non-patent Document (T. Astrup & S. Mullertz, The fibrin plate method for estimating fibrinolytic activity, Arch. Biochem. Biophys., 40: 346-351, 1952), a fibrin plate was prepared, and comparison of the dissolution activity was carried out by the fibrin plate method.

Fibrinogen (Bovine Fraction I-S, Sigma-Aldrich Co.) was dissolved in borate saline buffer (pH 7.8: BSB) to a final concentration of 0.5%. To 10 ml of this solution, 0.5 ml of thrombin (for clinical use, Fuji Pharma Co., Ltd.) was added, to prepare a fibrin plate.

Measurement of the area of dissolution was carried out by placing 30 µl of each measurement sample on the plate and measuring the area of the dissolved zone which appeared after 4 hours of incubation at 37° C. Further, a calibration curve for trypsin (Bovine, Sigma-Aldrich Co.), which is a protease, was prepared, and unit conversion was carried out to determine the specific activity based on the protein amount in each measurement sample. The results are shown in Table 8 below.

TABLE 8

|  | Dissolved area (mm²) | Activity in trypsin units (U/ml) | Protein amount (mg/ml) | Specific activity (U/mg) |
| --- | --- | --- | --- | --- |
| Example 2 | 243.4 | 351.7 | 6.9 | 51.0 |
| Comparative Example 5 | 207.4 | 246.6 | 7.3 | 33.8 |

As is evident from Table 7 and Table 8 above, in both the synthetic amide substrate degradation method and the fibrin plate method, the specific activity of the enzyme was about twice higher in the cases where the environment uncomfortable to earthworms was formed by addition of magnesium chloride (metal chloride) and lactic acid (hydroxycarboxylic acid) in that order, compared to the cases where these were added in the reverse order. Thus, it could be confirmed that, even in cases where a metal chloride(s) other than sodium chloride and a hydroxycarboxylic acid(s) other than citric acid are used, an earthworm powder having a high enzymatic activity can be obtained by adding the metal chloride(s) and the hydroxycarboxylic acid(s) in that order.

INDUSTRIAL APPLICABILITY

A dry earthworm powder produced by the method of the present invention is useful as an agent for blood pressure regulation, an anti-hyperlipemic agent, a therapeutic agent for diabetes mellitus, a thrombolytic agent and/or the like, similarly to dry earthworm powders produced by conventional methods. Further, by extracting this powder with pure water, an alcohol or the like and centrifuging the resulting solution, followed by fractionating the supernatant according to the molecular weight, the resulting product can be used as an effective component of a pharmaceutical, cosmetic or supplement.

The invention claimed is:
1. A method for producing a dry earthworm powder, comprising the steps of:
   (i) contacting a live earthworm (i.e., Oligochaeta) with a powder of a chloride(s) of at least one metal selected from the groups consisting of potassium, sodium, magnesium and calcium, and washing the live earthworm with water within 30 minutes of the contacting with the chloride(s);
   (ii) contacting the washed, live earthworm of step (i) with a powder of at least one hydroxycarboxylic acid and diluting the resulting mixture with water within 30 seconds of the contacting with the hydroxycarboxylic acid to produce an aqueous solution having a pH of 2 to 5 and then leaving the resulting mixture to stand for 3 to 180 minutes and washing the live earthworm with water;
   (iii) grinding the washed, live earthworm of step (ii) to produce a ground product;
   (iv) rapidly freezing the ground product to −18° C. to −35° C.; and
   (v) freeze-drying the frozen ground product.
2. The method for producing dry earthworm powder according to claim 1, wherein said live earthworm is left to stand in a bright place for 10 to 50 hours and dirt attached to the body surface is peeled off, before step (i).
3. The method for producing dry earthworm powder according to claim 1, wherein said freeze-drying is carried out by freezing said ground product at −18° C. to −35° C. for 20 to 240 hours and then freeze-drying resulting product under vacuum.

4. The method for producing dry earthworm powder according to claim 1, wherein said chloride of at least one metal is sodium chloride.

5. The method for producing dry earthworm powder according to claim 1, wherein said at least one hydroxycarboxylic acid is selected from the group consisting of acetic acid, malic acid, citric acid, lactic acid, malonic acid and succinic acid.

6. The method for producing dry earthworm powder according to claim 1, wherein the total length of time spent for the steps of (i) to (iii) is not more than 240 minutes.

7. A method for producing a dry earthworm powder, comprising the steps of:
(i) contacting a live earthworm (i.e., *Oligochaeta*) with a powder of a chloride(s) of at least one metal selected from the groups consisting of potassium, sodium, magnesium and calcium, and washing the live earthworm with water within 30 minutes of the contacting with the chloride(s);
(ii) soaking the washed, live earthworm of step (i) in an aqueous solution of at least one hydroxycarboxylic acid having a pH of 2 to 5 and then leaving the resulting mixture to stand for 3 to 180 minutes and washing the live earthworm with water;
(iii) grinding the washed, live earthworm of step (ii) to produce a ground product;
(iv) rapidly freezing the ground product to −18° C. to −35° C.; and
(v) freeze-drying the frozen ground product.

8. The method for producing dry earthworm powder according to claim 7, wherein said live earthworm is left to stand in a bright place for 10 to 50 hours and dirt attached to the body surface is peeled off, before step (i).

9. The method for producing dry earthworm powder according to claim 7, wherein said freeze-drying is carried out by freezing said ground product at −18° C. to −35° C. for 20 to 240 hours and then freeze-drying the resulting product under vacuum.

10. The method for producing dry earthworm powder according to claim 7, wherein said chloride of at least one metal is sodium chloride.

11. The method for producing dry earthworm powder according to claim 7, wherein said at least one hydroxycarboxylic acid, is selected from the group consisting of acetic acid, malic acid, citric acid, lactic acid, malonic acid and succinic acid.

12. The method for producing dry earthworm powder according to claim 7, wherein the total length of time spent for the steps of (i) to (iii) is not more than 240 minutes.

* * * * *